US011697576B2

(12) United States Patent
Greilinger et al.

(10) Patent No.: US 11,697,576 B2
(45) Date of Patent: Jul. 11, 2023

(54) TELESCOPIC LIFTING UNIT (71) Applicant: EWELLIX AB, Goeteborg (SE)

(72) Inventors: Daniel Greilinger, Rothenfluh (CH);
Christoph Riehl, Leymen (FR);
Marcel Soltermann, Sankt Pantaleon
(CH)

(73) Assignee: Ewellix AB, Goeteborg (SE)

( * ) Notice: Subject to any disclaimer, the term of this patent is extended or adjusted under 35 U.S.C. 154(b) by 609 days.

(21) Appl. No.: 16/684,032

(22) Filed: Nov. 14, 2019

(65) Prior Publication Data

US 2020/0148516 A1 May 14, 2020

(51) Int. Cl.
B66F 3/38 (2006.01)
A61B 6/00 (2006.01)
B66F 3/10 (2006.01)
B66F 3/44 (2006.01)

(52) U.S. Cl.
CPC .............. *B66F 3/38* (2013.01); *A61B 6/4405* (2013.01); *B66F 3/10* (2013.01); *B66F 3/44* (2013.01)

(58) Field of Classification Search
CPC .... B66F 7/02; B66F 7/025; B66F 7/14; B66F 7/28; B66F 3/38; B66F 3/10; B66F 3/08; B66F 3/28; A61B 6/4405
See application file for complete search history.

(56) References Cited

U.S. PATENT DOCUMENTS

| 10,674,978 | B2 | 6/2020 | Takemoto et al. |
| 2011/0243309 | A1 | 10/2011 | Weijang |
| 2011/0249807 | A1* | 10/2011 | Dirisio ................... A61B 6/447 378/198 |
| 2020/0069269 | A1* | 3/2020 | Han ..................... A61B 6/4405 |
| 2020/0187885 | A1* | 6/2020 | Tang ..................... A61B 6/447 |

FOREIGN PATENT DOCUMENTS

| CN | 102204824 A | 10/2011 |
| CN | 205973630 U | 2/2017 |
| CN | 206244324 U | 6/2017 |
| CN | 108439259 A | 8/2018 |
| CN | 108778132 A | 11/2018 |
| JP | H04122243 A | 4/1992 |

* cited by examiner

Primary Examiner — Tyrone V Hall, Jr.
(74) Attorney, Agent, or Firm — Laurence A. Greenberg; Werner H. Stemer; Ralph E. Locher (57) ABSTRACT A telescopic lifting unit with a first segment, a second segment, and a third segment. The first and second segments may be displaced relative to one another, and the second and third segments may be displaced relative to one another. The first and second segments may be moved relative to one another by a motor unit, and the second and third segments may be moved relative to one another by a cable hoist.

12 Claims, 12 Drawing Sheets

TELESCOPIC LIFTING UNIT

CROSS-REFERENCE TO RELATED APPLICATION

This application claims the priority, under 35 U.S.C. § 119, of German patent application DE 10 2018 219 404, filed Nov. 14, 2018; the prior application is herewith incorporated by reference in its entirety.

BACKGROUND OF THE INVENTION

Field of the Invention

The present invention relates to a telescopic lifting unit with a first segment, a second segment and a third segment. The first and second segments may be displaced relative to one another and the second and third segments may be displaced relative to one another.

In various technical fields, loads are moved using a telescopic lifting column or other lever means. This is also the case for medical equipment; such as for example X-ray equipment. Depending on the weight of the load, such movement is only possible if there is sufficient power available from a motor-driven drive train, or from an operator who moves the load manually. Suitable means that compensate the weight force, for example gas pressure springs, may significantly reduce the power required for this movement. Additionally, faster movements may also be achieved by using suitable means. Systems that offer these advantages, however, usually require considerable space and are structurally complex.

This is particularly disadvantageous for mobile equipment, especially mobile X-ray equipment, because the user must be able to move such equipment. Heretofore, the telescopic lifting columns used have had the drawback that they are very tall when built, and may obstruct the user's view when moving the equipment.

SUMMARY OF THE INVENTION

It is accordingly an object of the invention to provide a telescopic lifting unit, which overcomes the above-mentioned and other disadvantages of the heretofore-known devices and methods of this general type and which provides for a lifting unit that may move a load in a straightforward manner, while at the same time requiring less space.

With the foregoing and other objects in view there is provided, in accordance with the invention, a telescopic lifting unit, comprising:

a first segment, a second segment, and a third segment;
said first and second segments being mounted for displacement relative to one another;
said second and third segments being mounted for displacement relative to one another;
a motor unit configured to move said first and second segments relative to one another; and
a cable hoist configured to move said second and third segments relative to one another.

In other words, the telescopic lifting unit has a first segment, a second segment and a third segment, wherein the first and second segments may be displaced relative to one another and the second and third segments may be displaced relative to one another. To enable the segments to be easily moved relative to one another, the first segment and second segment may be moved relative to one another by a motor unit. Because a motor unit makes possible simple, fast movement with little effort, but at the same time requires a relatively large space, the second and third segments may be moved relative to one another not by a motor unit, but by a cable hoist instead. A cable hoist affords a more space-saving method of displacing the segments relative to one another. In this way, the advantages of a motor-driven drive train and a cable-driven drive train are combined. Consequently, there are realized both a rapid displacement of the segments relative to one another by the motor unit, and a space-saving movement of the segments relative to one another by the cable hoist.

In one embodiment, the motor unit interacts with a spindle to convert a rotational movement of the motor of the motor unit into a translational movement between the first and second segments. For example, the first and second segments may be designed as respective columns that are fastened to or inside one another, and are movable relative to one another. The spindle of the motor unit may be arranged inside one of the columns, with a counterpart, for example a sleeve, arranged in the other column. When there is a rotational movement of the motor, the spindle may be retracted or extended into the sleeve to allow a translational movement between the first and second segments. The spindle is connected to the first segment, for example via the motor unit arranged in this segment, and also to the second segment. Preferably, the sleeve is rotated rather than the spindle, thus reducing the noise generated.

The telescopic lifting unit may in particular be part of a mobile medical apparatus, such as a mobile X-ray apparatus. One of the segments may be fastened to a mobile stand that may be designed as a mobile wheel stand. The telescopic lifting unit proposed herein makes it possible to give the medical apparatus a compact configuration. This prevents the telescopic lifting unit from obstructing the user's view when the equipment is being moved. In addition, the motor unit may be used to quickly adjust the height for a location where the medical apparatus is to be used, i.e. a coarse adjustment; in contrast, the cable hoist allows a fine adjustment of the height for the location where the device is to be used.

If the telescopic lifting unit is part of a mobile medical apparatus, the load may likewise be part of that medical apparatus and may be, for example, an X-ray head. This load may be fastened to one of the segments. In particular, the load-bearing segment may have a linear guide for displacing the load. In this way, in addition to an extension movement of the segments to one another, preferably in a first direction, for example a vertical direction, the load may also be displaced in a direction perpendicular to the first direction, for example a horizontal direction.

According to one embodiment, the motions of the first and second segments are synchronized relative to one another and the motions of the second and third segment are synchronized relative to one another. This may readily be accomplished by using a cable guide of the cable hoist. In particular, at least two guide rollers are used that act in opposite directions. The height covered by the movement of the first and second segments relative to one another, and the height covered by the movement of the second and third segments relative to one another, are thus substantially the same.

According to another embodiment, the motor unit has a first displacement speed and the cable hoist has a second displacement speed. In particular, the first displacement speed may be greater than the second displacement speed. According to this embodiment, the extension of a first part of the telescopic lifting unit may be done very quickly by the motor unit, while in contrast, the cable hoist moves a second part of the telescopic lifting unit more slowly, but also more precisely. However, the cable hoist allows a more precise extension of the second part of the telescopic lifting unit compared to the motor unit. The first part of the telescopic lifting unit may be the displacement range of the second segment relative to the first segment and the second part of the telescopic lifting unit may be the displacement range of the third segment relative to the second segment.

The cable hoist for displacing the second and third segments relative to one another may be operated in different ways. For example, the cable hoist may be moved by hand, by motor or at least in a motor-assisted manner. If the cable hoist is moved by motor, the second displacement speed may be approximated to the first displacement speed. If the cable hoist is motor-assisted, various sensors may be used to determine the weight of the load to be moved and to reduce this weight for the user who seeks to operate the cable hoist manually. In this way, the motor assistance reduces the weight for the user. In particular, this weight compensation for the third segment relative to the second segment may be achieved by a spring element, for example a gas spring, and a pulley block, which may consist of a plurality of rollers. The weight compensation mechanism for the third segment may be arranged entirely within the second segment. In this way, the entire lifting unit may be made very compact.

Both the motor unit and the cable hoist, or one of them, may have a weight compensation means. The weight compensation means may, for example, be a spring element such as a gas spring. The weight compensation means makes it possible to reduce the mass to be moved both for the motor unit and for the cable hoist. Moreover, the weight compensation means of the cable hoist may be adapted to accommodate the cable of the cable hoist. If the entire lifting unit is in a parking position or moving to a parking position, i.e. the segments are pushed together, the weight compensation means may act as a kind of cable holder and accommodate excess cable. In the case of a gas spring, this may be done for example by tensioning the gas spring or extending the gas spring. The gas spring may keep the cable under tension, and thus may act as a brake at the same time.

In order to secure the position of the segments relative to one another, both the motor unit and the cable hoist may have a braking means. Such a braking means likewise ensures that the segments maintain their current position relative to one another in the event the respective drives fail. This prevents the load fastened to one of the segments from falling and damaging the telescopic lifting unit or the environment in the event of a failure of the various drives.

According to another embodiment, the telescopic lifting unit may have a force sensor. Via this force sensor, it may be detected that a user wants to move or displace the segments. The force sensor may then transmit a signal to the motor unit that initiates movement of the segments based on the signal. In this way, the force the user is required to exert may be reduced, because the intention to move may be detected and the movement may be implemented directly by the motor unit. The force sensor may for example be arranged on the cable hoist, or at a connection between the segments, or at any other suitable location.

Additional advantages and advantageous embodiments are set forth in the description, drawings and claims. In particular, the combinations of features indicated in the description and in the drawings are purely exemplary; the features may be present individually or may be combined in other ways.

Although the invention is illustrated and described herein as embodied in telescopic lifting unit, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
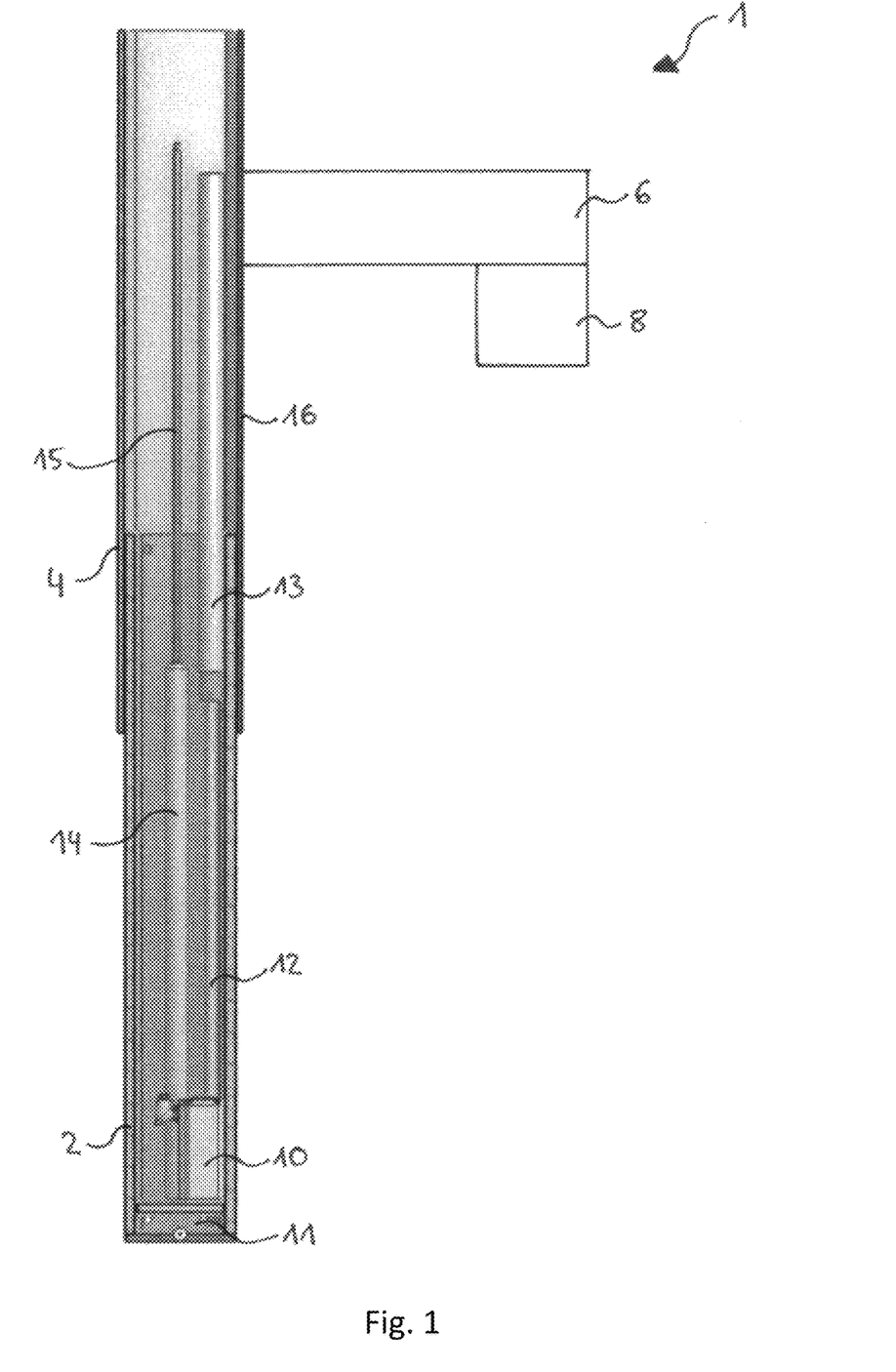
FIG. 1 a sectional view of a telescopic lifting unit.

Referring now to the drawing figures in detail, FIG. 1 shows a telescopic lifting unit 1 with a first segment 2, second segment 4, and third segment 6. In the embodiment shown, the first and second segments 2 and 4 are designed as columns, and the third segment 6 is displaceable along one side of the second segment 4. A load 8 may be fastened to the third segment 6. For example, the telescopic lifting unit 1 may be part of a medical apparatus, such as a mobile X-ray machine. The load may be, for example, an X-ray head. The telescopic lifting unit 1 may also be used for various other purposes that require displacement of segments relative to one another. If the telescopic lifting unit 1 is used for mobile purposes, the lowest segment, namely the first segment 2 in the embodiment shown, may be fastened to a mobile wheel stand.

To make it possible to extend the telescopic lifting unit 1, the first segment 2 and second segment 4 are displaceable relative to one another. The second segment 4 and third segment 6 are likewise displaceable relative to one another.

To enable a fast movement or extension of the lifting unit 1, movement between the first segment 2 and the second segment 4 is realized by a motor unit 10. The motor unit 10 may be arranged on a baseplate 11 of the first segment 2. Arranging the motor unit 10 inside the first segment 2 makes possible a compact configuration of the lifting unit 1. In the embodiment shown here, the first segment 2 is designed as an inner column, along which the second segment 4 slides. The third segment 6 is moved along a side face 16 of the second segment 4.

The motor unit 10 transmits a rotational movement to a spindle 12, which converts the rotational movement into a translational movement by retraction or extension into a sleeve 13. The translational movement causes the second segment 4 to move upward relative to the first segment 2. If the segments 2, 4 are retracted, the spindle 12 is located in the sleeve 13. If the segments 2, 4 are extended, the sleeve 13 is moved upward and the spindle 12 is located outside the sleeve 13. By means of the motor unit 10, a rapid movement is achieved. In particular, only two positions need to be controlled by the motor unit 10: fully retracted or fully extended. Accordingly, a very simple control is sufficient.

A gas spring 14 is furnished that serves as a weight compensation means in order to hold the second segment 4 in its extended position. In a retracted state of the segments 2, 4, a piston 15 of the gas spring 14 is arranged in a receptacle of the gas spring 14 that is designed for example as a cylinder, which is arranged in the first segment 2.

Figure 2:
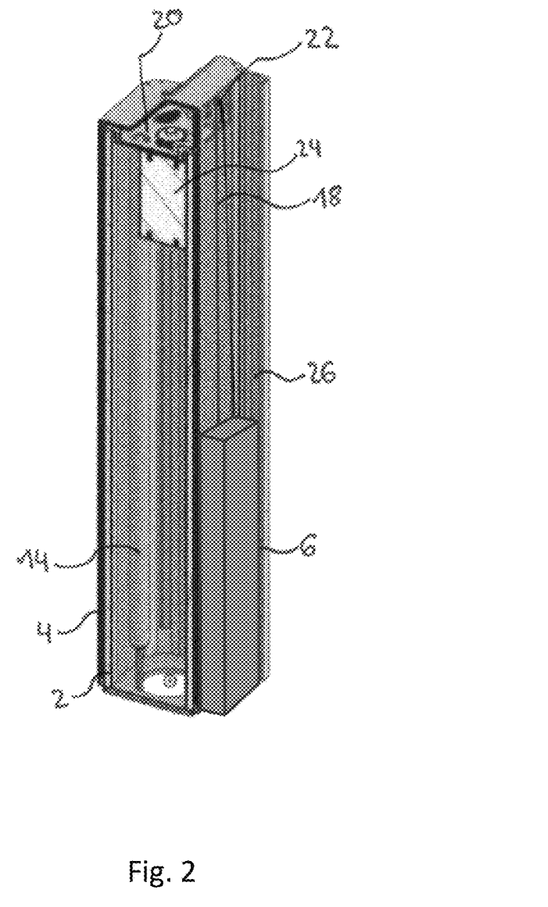
FIG. 2 a perspective sectional view of the telescopic lifting unit of FIG. 1 in a fully retracted state.
Figure 3:
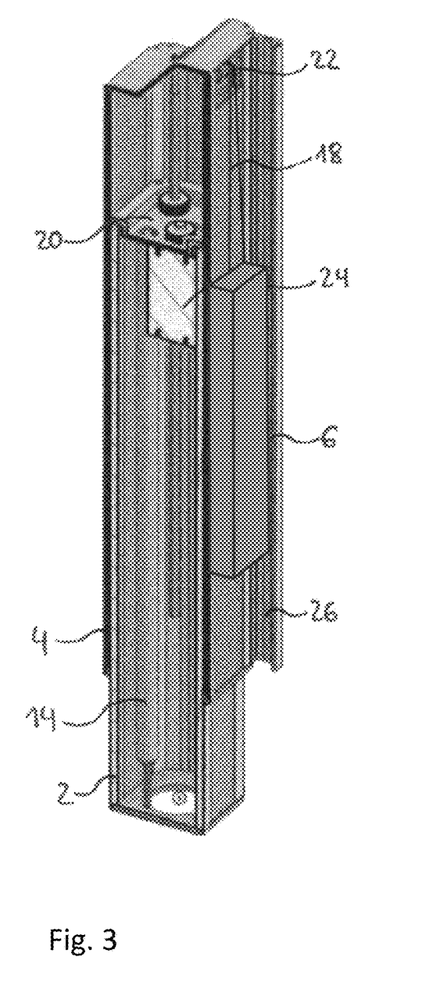
FIG. 3 a perspective sectional view of the telescopic lifting unit of FIG. 1 in a half-extended state.
Figure 4:
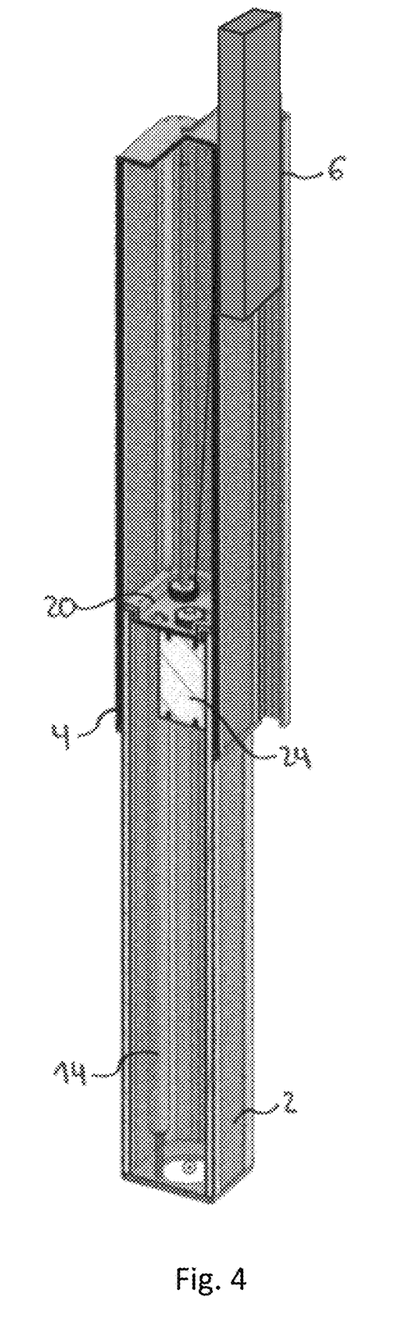
FIG. 4 a perspective sectional view of the telescopic lifting unit of FIG. 1 in a fully-extended state.
Figure 5:
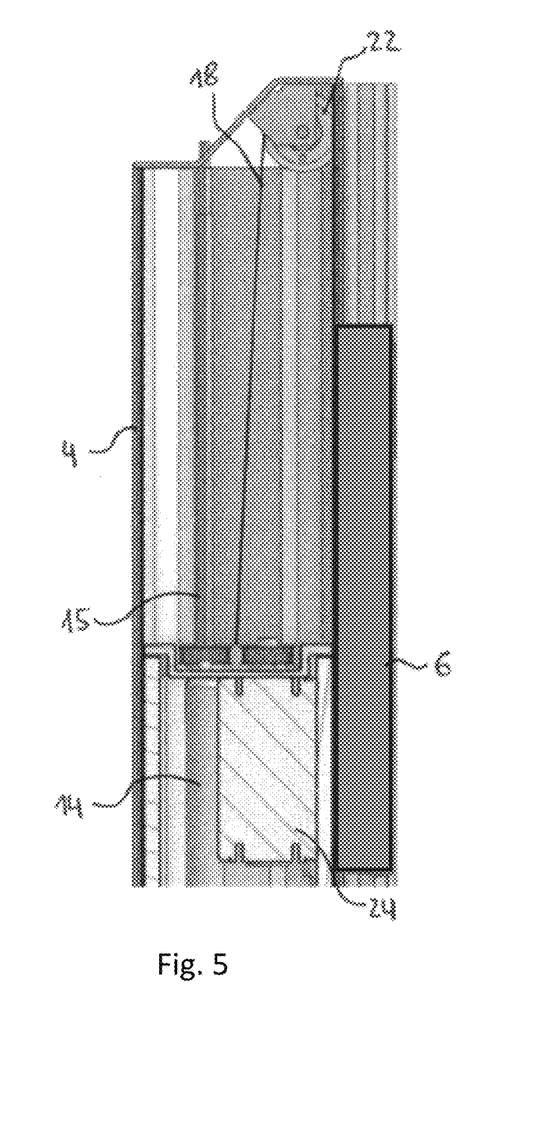
FIG. 5 a sectional view of the second and third segments of the telescopic lifting unit from FIG. 1.
Figure 6:
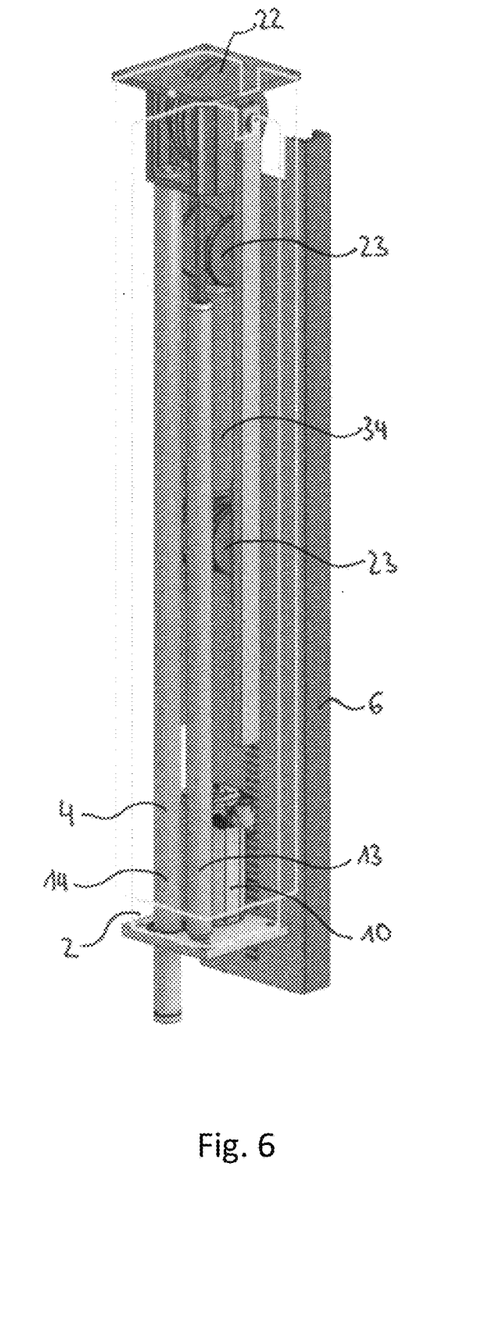
FIG. 6 a perspective view of the second and third segments of the telescopic lifting unit of FIG. 1.
Figure 7:
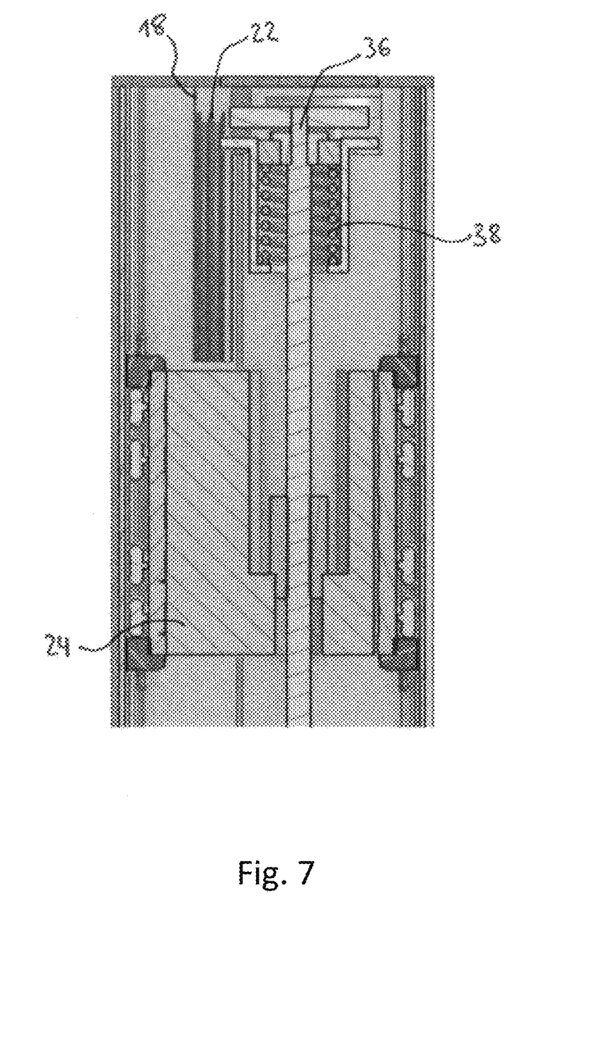
FIG. 7 a detail view of the cable hoist of the telescopic lifting unit that is illustrated in FIG. 1.

The movement between the second segment 4 and the third segment 6 is not realized by a rapid drive such as the motor unit 10 provides, but instead by a cable hoist 18, as shown in FIGS. 2 to 4 in different stages of extension of the second and third segments 4, 6 and also in detail in FIGS. 5 to 7.

The cable hoist 18 performs a slower drive or a slower movement, but allows a finer adjustment of the position of the third segment 6 relative to the second segment 4. The third segment 6 is connected to the second segment 4 via the cable hoist 18. In particular, a cable of the cable hoist 18 is fastened to a plate 20 between the first segment 2 and the second segment 4. The cable is connected between the plate 20 and the third segment 6 via a guide roller 22, as shown in FIG. 5. In addition, additional guide rollers 23 may be used to allow additional weight reduction and simplify the movement of the third segment 6.

FIG. 2 shows a fully retracted position of both the second segment 4 and the third segment 6. In FIG. 3, both segments 4, 6 are moved slightly upward. FIG. 4 shows a fully extended position of the second segment 4 relative to the first segment 2, and also a fully extended position of the third segment 6 relative to the second segment 4.

The second segment 4 is driven by a motor unit 10, as already described and shown in connection with FIG. 1. Likewise, the cable hoist 18 may be driven via a motor unit 24, as shown in FIGS. 2 to 7. The motor unit 24 may be arranged in the upper area of the first segment 2. The cable is connected to the motor unit 24, which controls a spindle 36 when the third segment 6 is displaced, the spindle being connected to the cable. Moreover, a spring element 38 may be used to compensate the weight of the load 8. In particular, the spring element 38 may apply a force to the spindle 36 to reduce the weight of the load 8 on the guide roller 22 or the cable.

As FIG. 7 shows, a gas spring 34 may likewise be used for weight compensation for the movement of the third segment 6. The gas springs 14, 34 may act as brakes at the same time. This serves purposes of safety among other things, because in an emergency the gas springs 14, 34 may hold the current position of the individual segments 2, 4, 6. In addition, in normal operation, gas springs 14, 34 may also be used in order to hold the position of segments 2, 4, 6.

The motor units 10, 24 may each respectively have a brake (not shown) in order to hold the position of the respective segment 4, 6. The cable hoist 18 may be additionally secured, for example against cable breakage, by using two redundant cables, or by additionally incorporating a mechanism that holds the third segment 6 in position if the cable breaks. This may be done, for example, via such a brake or via the gas spring 34.

Figure 8:
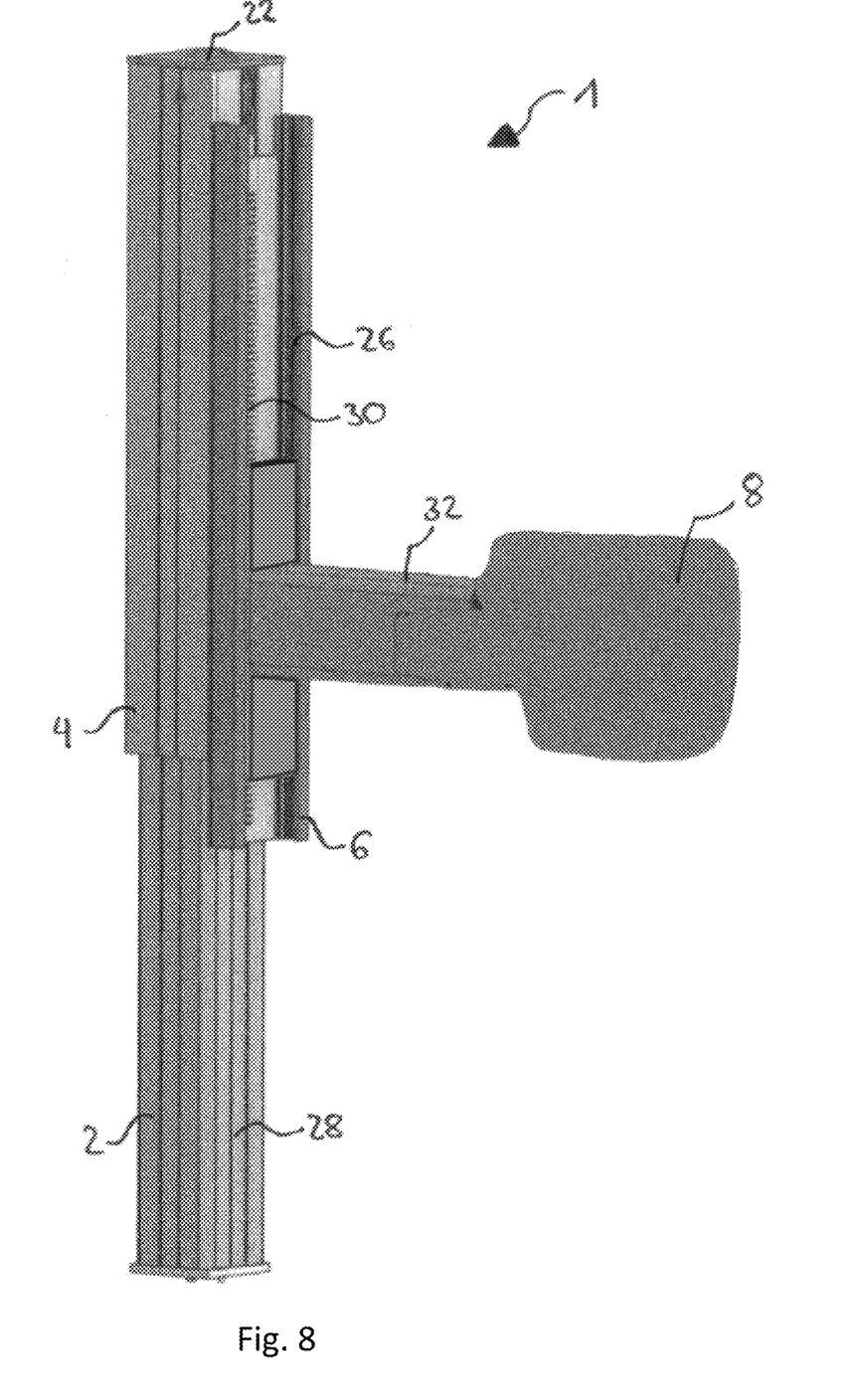
FIG. 8 a perspective view of the telescopic lifting unit from FIG. 1.

FIG. 8 shows another perspective view of the lifting unit 1. As shown here, the third segment 6 may be displaced relative to the second segment 4 in a rail guide 26. The first segment 2 likewise has guide rails 28 for displacing the second segment 4 relative to the first segment 2. The second segment 4 may also have detents 30 in the rail guide 26, in which the third segment 6 may engage when not in motion. The detents 30 allow the third segment 6 to be displaced in stages. The third segment 6 may also have a linear guide 32 on which the load 8, in this case an X-ray head, may be displaced horizontally.

Figure 9:
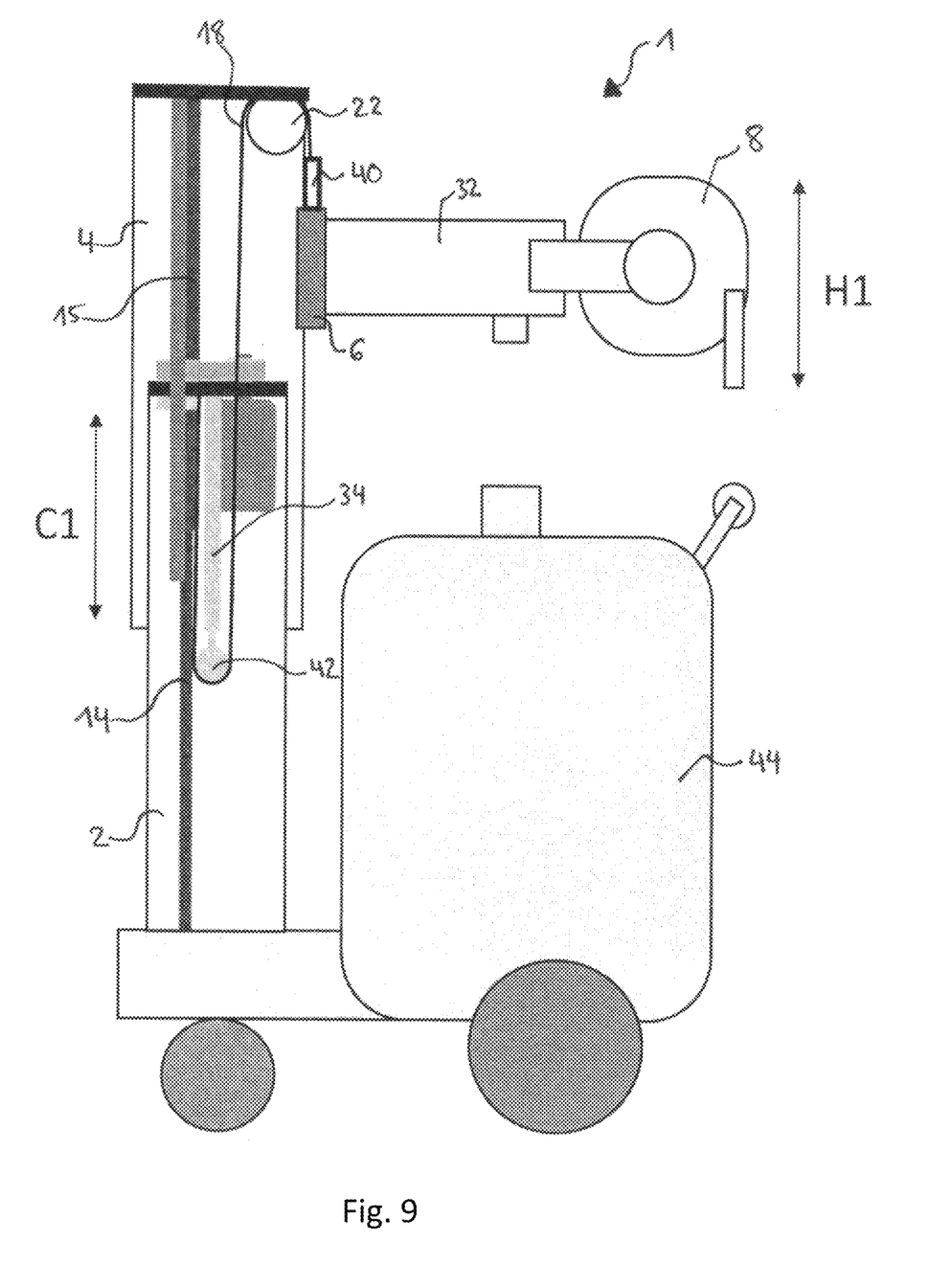
FIG. 9 a perspective view of another embodiment of the telescopic lifting unit from FIG. 1.

Another embodiment of the lifting unit 1 is shown in FIG. 9. As shown here, the segment 2 may be arranged on a mobile wheel stand 44.

In the embodiment shown in FIG. 9, the segments 2, 3 and 4 may be moved synchronously with one another. If segment 4 is displaced by height C1 with respect to segment 2, the segment 6 is simultaneously displaced by height H1 with respect to segment 4, and the heights C1 and H1 are the same.

In this case the motor unit 10 is arranged at the upper end of the segment 2, not at the bottom of the segment 2. Preferably, it is the sleeve 13 that is controlled (i.e. rotated) rather than the spindle 12.

The telescopic lifting unit 1 may also have a force sensor 40. In the embodiment shown here, the cable hoist 18 is coupled with the force sensor 40. Alternatively, the force sensor 40 may also be arranged at any other suitable location. The force sensor 40 may detect that a user wants to change the position of the load 8, and may transmit this information to the motor unit 10 as a signal. Thus, the motor unit 10 may be controlled in advance, based on the user's intention to move. In this way, the force that the user must apply may be reduced.

To operate the cable hoist 18 synchronously with the motor unit 10, one end of the cable of the cable hoist 18 is fastened to the upper end of the segment 2. The gas spring 34 here serves not only for weight compensation, but also to keep the cable of the cable hoist 18 under tension and to hold the segment 6 in position. For this purpose, the gas spring 34 has a guide roller 42. The guide roller 42 may accommodate excess cable by extending the gas spring 34 downward.

If the user moves the segment 6 from its position, two different reactions may occur, depending on the damping properties. If there is little damping of the gas spring 34, the segment 6 may maintain its vertical position until the gas spring 34 is retracted again. If, on the other hand, the gas spring 34 is damped strongly, the segment 6 immediately moves upward.

Figure 10:
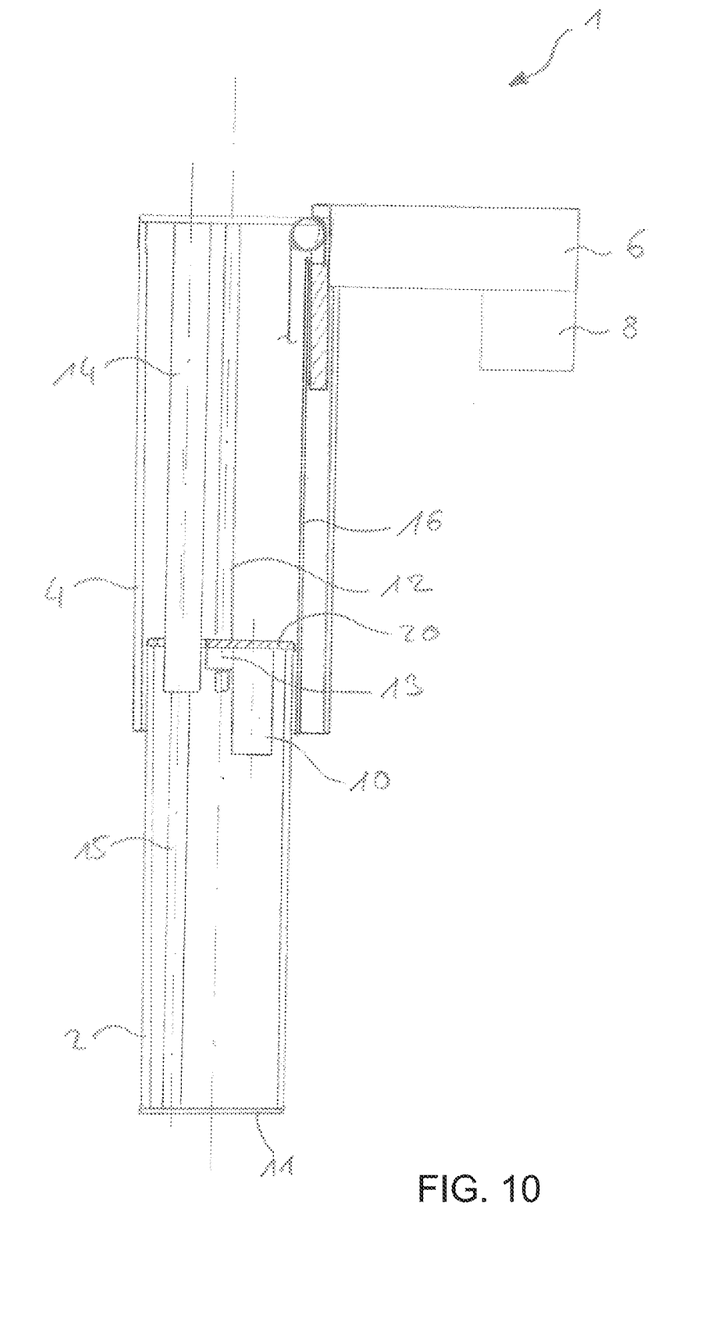
FIG. 10 a sectional view of another example of a telescopic lifting unit.

FIG. 10 shows another example of a telescopic lifting unit 1 with a first segment 2, a second segment 4 and a third segment 6, wherein the segments 2, 4, 6 are mounted so as to be displaceable, and in particular at least partially telescopically displaceable, relative to one another. In the example shown, in particular, the second segment 4 is telescopically displaceable relative to the first segment 2, and the third segment 6 is displaceable along a side face 16 of the second segment 4. In this case as well, a load 8, for example an X-ray head, may be fastened to the third segment 6.

To displace the second segment 4 relative to the first segment 2, a motor unit 10 is furnished. In contrast to the example shown in FIG. 1, in the example shown in FIG. 10, the motor unit 10 is arranged at an upper end of the first segment 2, facing a lower end of the first segment 2 that is defined by a baseplate 11. In this case, the motor unit 10 may in particular be mounted on a plate 20 that closes off the first segment 2 at the upper end.

The motor unit 10 is preferably configured to set in rotation a sleeve 13 that surrounds a spindle 12. The sleeve 13 in this case preferably has an inner threading that is in engagement with an outer threading of the spindle 12. Thus, as a result of the rotation of the sleeve 13, a translation of the spindle 12 may be generated along a longitudinal axis of the lifting unit 1, and in particular of the segments 2, 4, 6.

In this case, one end of the spindle 12 is connected to the second segment 4, in particular at an upper end of the second segment 4 that faces away from the baseplate 11 of the first segment 2. As a result of the rotational movement that the sleeve 13 transmits to the motor unit 10, a rapid translational movement of the second segment 4 and the third segment 6 connected thereto, and of the load 8, may be achieved.

Arranging the motor unit 10 at the upper end of the first segment 2 has the advantage that a particularly short or compact sleeve 13 may be used. In contrast to the example shown in FIG. 1, in particular, there is no need for a sleeve 13 that extends substantially through the entire interior of the first segment 2; as a result, the lifting unit 1 may be made more compact overall. In addition, the force acting on the sleeve 13, in particular torsional load, may be reduced by a compact sleeve 13.

Also in the example shown in FIG. 10, a gas spring 14 is furnished as a weight compensation means for holding the second segment 4 in an extended position relative to the first segment 2. In the retracted state of the segments 2, 4, a piston 15 of the gas spring 14 is accommodated, preferably substantially completely, in a cylinder of the gas spring 14 that is designed as a receptacle. In this case, the cylinder is connected to the second segment 4, preferably analogously to the spindle 12, and in particular is connected at an upper end of the first segment that faces away from the baseplate 11. As a result, the cylinder moves upward when the second segment 4 is extended.

The cylinder of the gas spring 14 is preferably arranged substantially completely inside the first segment 2 in the retracted state of the segments 2, 4. The plate 20 in this case preferably has a bore that the gas spring 14, in particular the cylinder, passes through.

The piston 15 is preferably connected to the first segment 2, in particular to the baseplate 11 or at least in the vicinity of the baseplate 11, so that the piston 15 is pulled out of the cylinder when the second segment 4 is extended.

Figure 11:
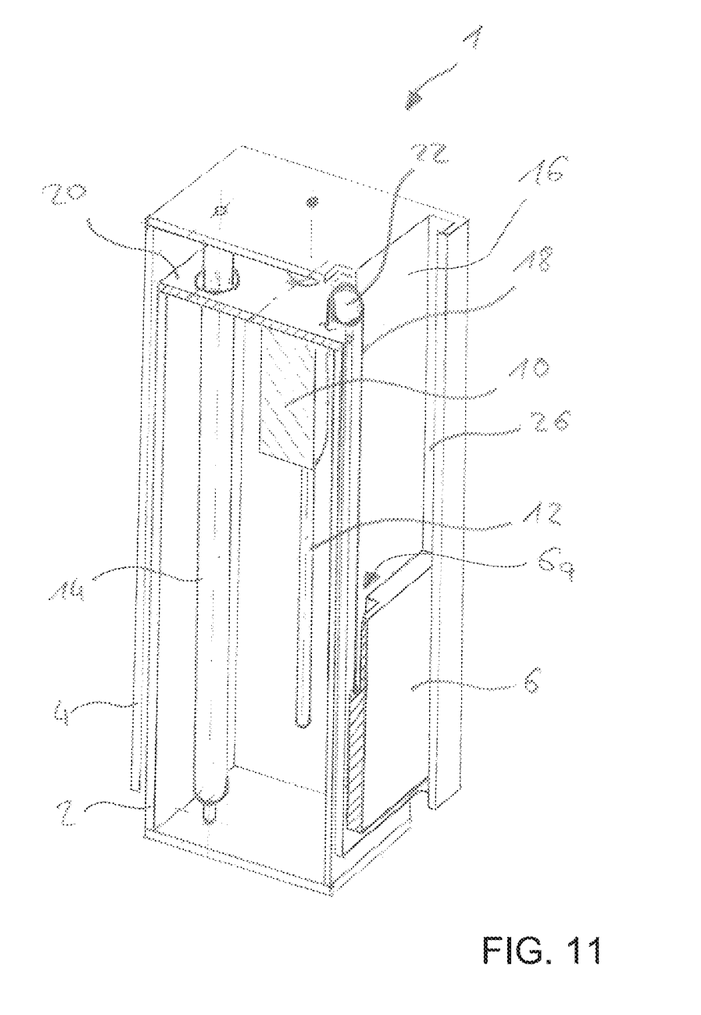
FIG. 11 a perspective sectional view of the telescopic lifting unit of FIG. 10 in a fully-retracted state.
Figure 12:
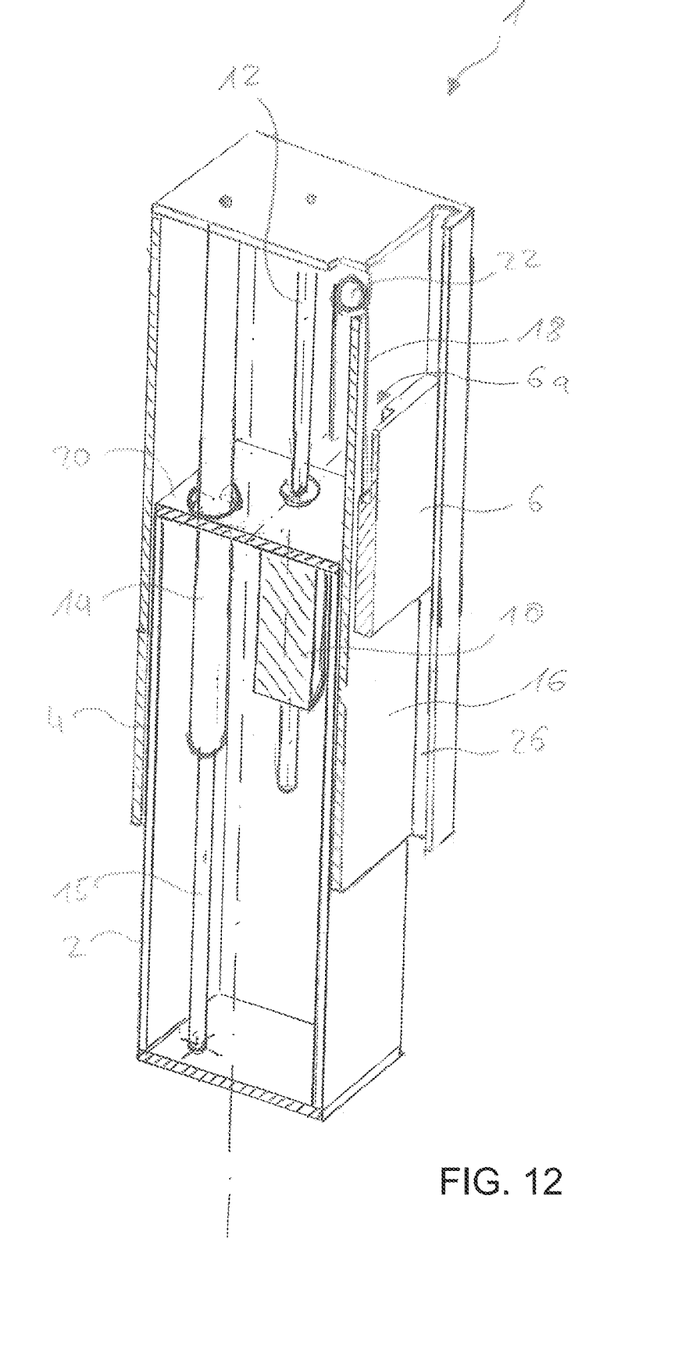
FIG. 12 a perspective sectional view of the telescopic lifting unit of FIG. 10 in a half-extended state.

FIG. 11 shows a perspective sectional view of the telescopic lifting unit 1 of FIG. 10 in a fully-retracted state. In this case, the second segment 4 and the third segment 6 are substantially not displaced relative to the first segment 2, and in particular the second segment 4 is not extended relative to the first segment 2. In FIG. 12, the lifting unit 1 of FIG. 10 is shown in a half-extended state in which the second and third segments 4, 6 are displaced, in particular extended, slightly upwards. Finally, FIG. 13 shows a lifting unit 1 from FIG. 10 in a fully-extended state.

Figure 13:
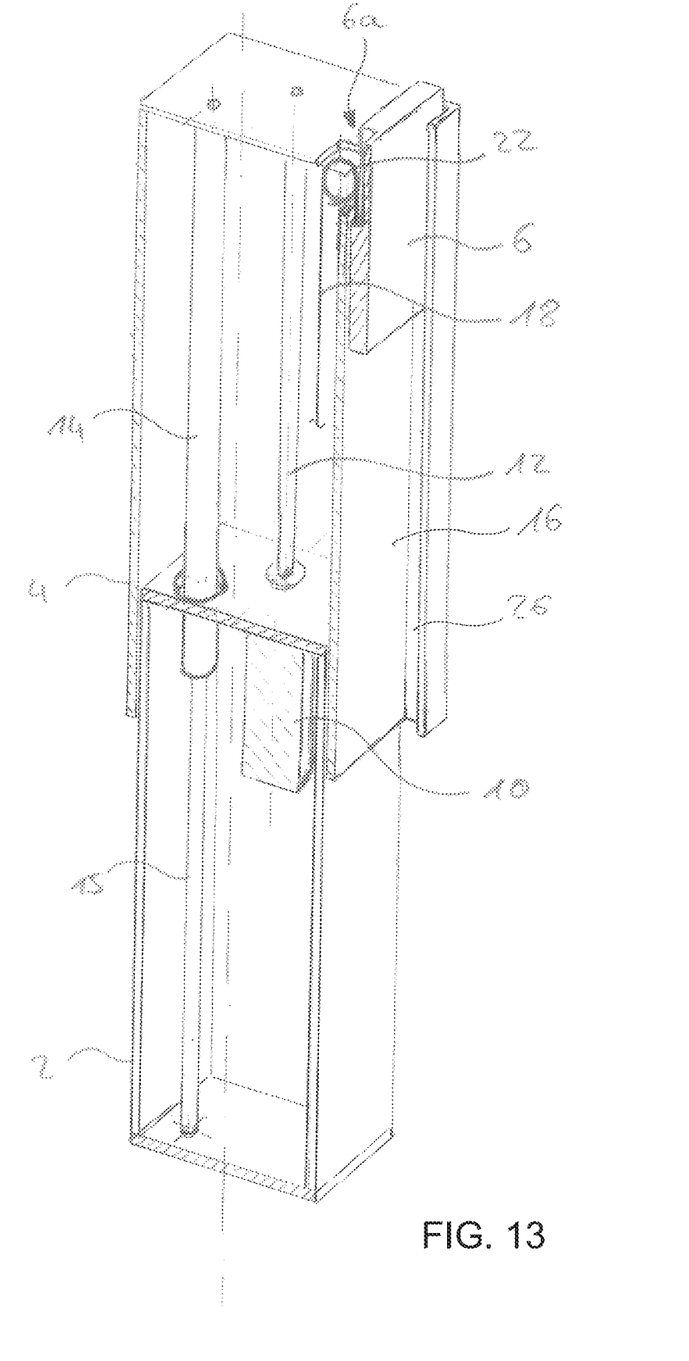
FIG. 13 a perspective sectional view of the telescopic lifting unit of FIG. 10 in a fully-extended state.

As is readily apparent from FIGS. 11, 12 and 13, the third segment 6 is preferably displaced along a side wall of the second segment 4 via a cable hoist 18. To operate the cable hoist 18, the cable of the cable hoist 18 may be fastened to the plate 20 at the upper end of the first segment 2. Alternatively, it is also possible to arrange a motor on the plate 20, and this motor may operate the cable hoist 18. For reasons of clarity, however, this motor is not shown in FIGS. 11,12 and 13.

When displaced relative to the second segment 4, the third segment 6 is preferably guided by means of a rail guide 26. In this case, at least a part of the third segment 6 is arranged between two guide rails of the rail guide 26; only one of the two guide rails is shown in the sectional view in FIGS. 11, 12 and 13. The guide rails surround the third segment 6 or at least part of the third segment 6 at least in sections, such that the third segment 6 may move only in a longitudinal direction of the lifting unit 1, in particular the longitudinal direction of the second segment 4. For this purpose, the third segment 6 or at least a part of the third segment 6 may be designed as a carriage that is movably mounted in the rail guide 26.

To be able to exert effective force on the third segment 6 by means of the cable hoist 18, the third segment 6 preferably has a cable recess 6a, in which the cable of the cable hoist 18 is connected to the third segment 6. In other words, the connection between the cable and the third segment 6 is preferably protected by being located inside the cable recess 6a. As a result, the cable of the cable hoist 18 may run substantially parallel to the side wall 16 and rail guide 26.

Figure 14:
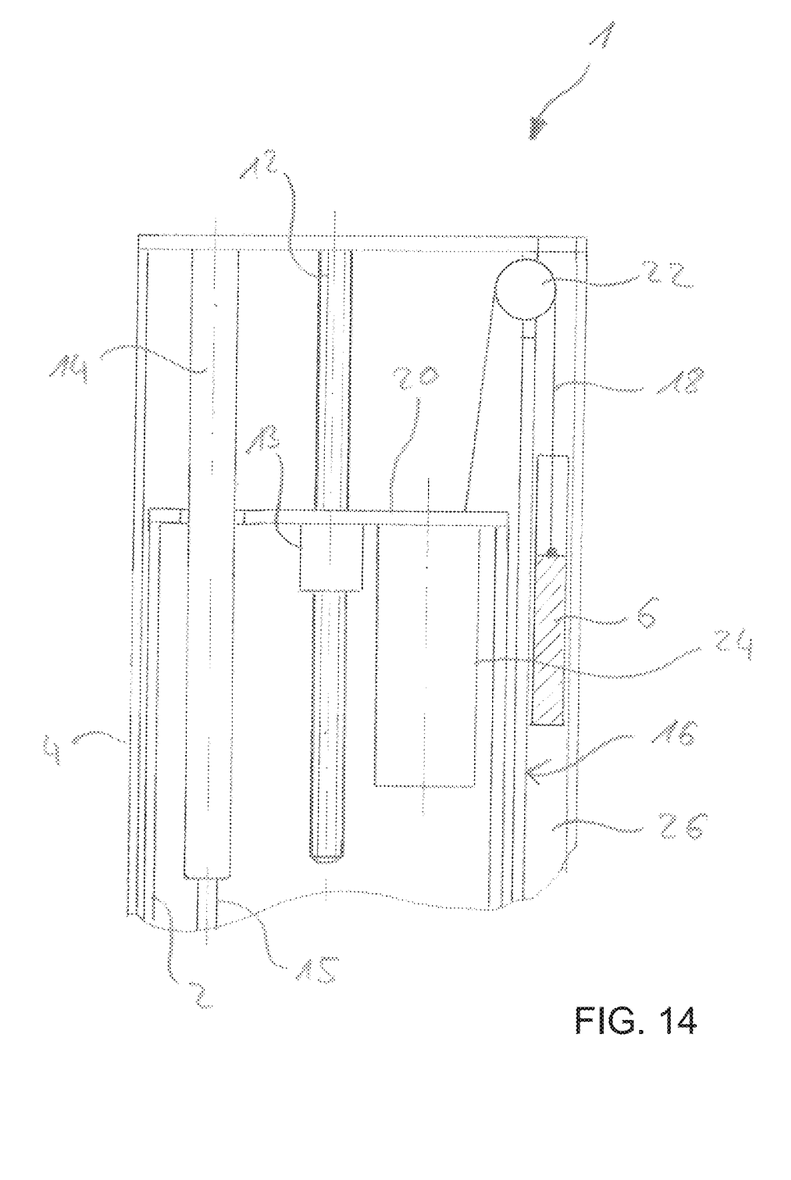
FIG. 14 a sectional view of the second and third segments of the telescopic lifting unit from FIG. 10.

FIG. 14 shows a sectional view of the second and third segments 4, 6 of the telescopic lifting unit 1 from FIG. 10. In this case it is readily apparent how the third segment 6 is mounted so as to be displaceable along the side wall 16 of the second segment 4, by means of the cable hoist 18 and a guide roller 22, which guides the cable of the cable hoist 18 at the upper end of the second segment 4. In this case, the third segment 6, or at least a part thereof, preferably moves along the side wall 16 with the aid of the rail guide 26. In this case, the guide roller 22 is preferably formed and/or arranged such that it does not protrude laterally beyond the rail guide 26. The guide roller 22 may in particular be designed and/or arranged such that the cable of the cable hoist 18 runs substantially parallel to the rail guide 26 between the steering wheel 22 and the third segment 6.

To operate the cable hoist 18, a motor 24 is preferably furnished that is arranged at the upper end of the first segment, in particular the plate 20, which defines the upper end of the first segment. For reasons of clarity, FIG. 14 does not show the motor unit for generating the rotational movement of the sleeve 13.

Figure 15:
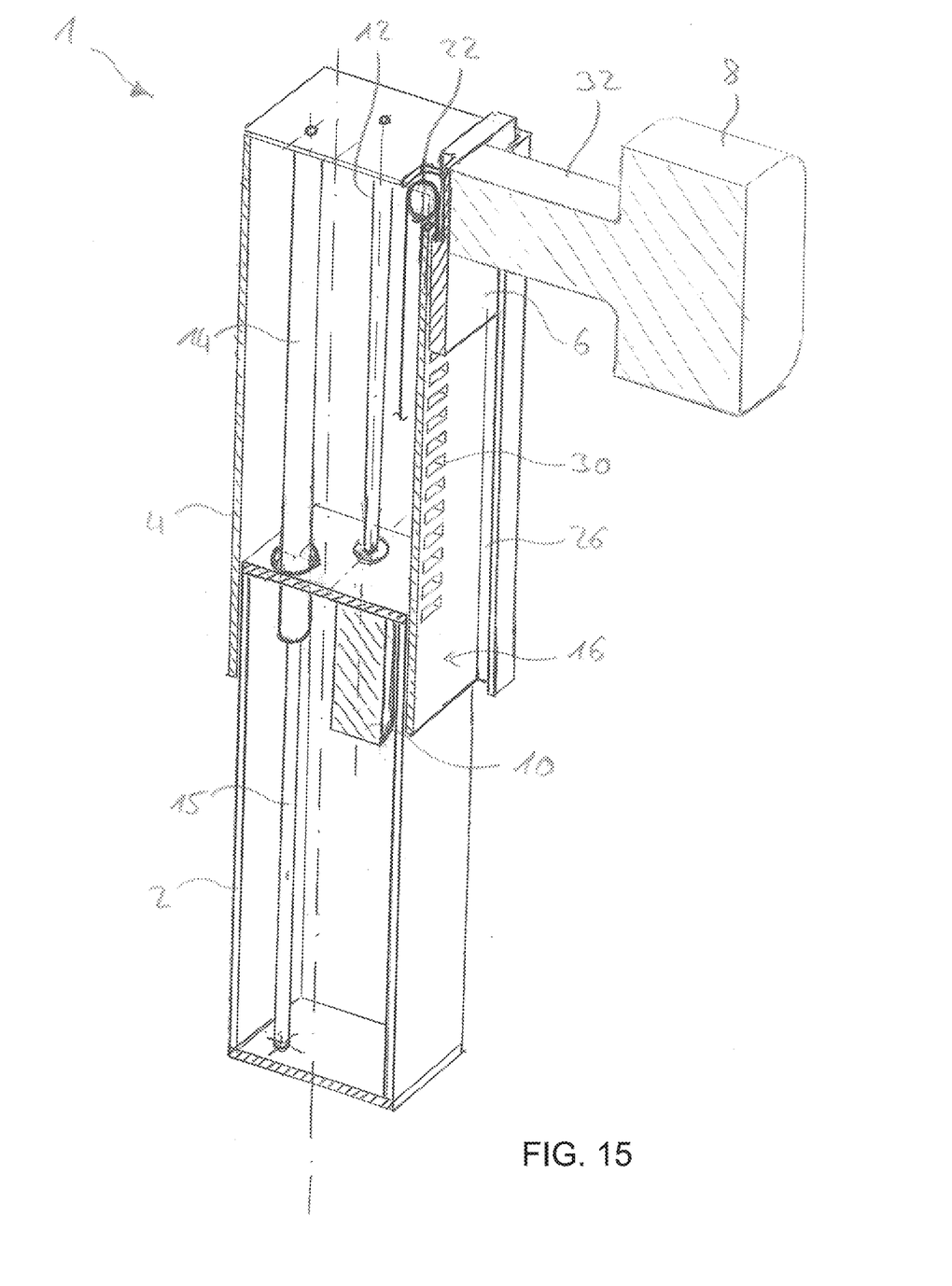
FIG. 15 a perspective view of the telescopic lifting unit from FIG. 10.

FIG. 15 shows a perspective view of the telescopic lifting unit 1 from FIG. 10. Here the detents 30 of the second segment 4, which allow a gradual displacement of the segment 6, are particularly apparent. The detents 30 in this case are arranged in the rail guide 26, in particular between two guide rails of the rail guide 26. The detents 30 may be formed, for example, by recesses in the second segment 4, in particular in the side wall 16 of the second segment. Such a configuration of the detents 30 makes possible a particularly robust latching mechanism.

In summary, the telescopic lifting unit proposed herein allows a compact design to be achieved, because the different drives, namely the motor unit and the cable hoist, may be fully integrated into the telescopic lifting unit. By the combination of two different drives, it is possible to achieve both a very fast movement, namely by the motor unit, and a precise adjustment of the position, namely by the cable hoist. Furthermore, the combination of two movement ranges, i.e. the displacement of the first and second segments relative to one another and the displacement of the second and third segments relative to one another, enables a large range of adjustment of the entire telescopic lifting unit.

The following is a summary list of reference numerals and the corresponding structure used in the above description of the invention:

1 Telescopic lifting unit
2 First segment
4 Second segment
6 Third segment
6a Cable recess
8 Load
10 Motor unit
11 Baseplate
12 Spindle
13 Sleeve
14 Gas spring
15 Piston
16 Side face
18 Cable hoist
20 Plate
22 Guide roller
24 Motor
26 Rail guide
28 Guide rails
30 Detents
32 Linear guide
34 Gas spring
36 Spindle
38 Spring element
40 Force sensor
42 Guide roller
44 Stand
C1, H1 Height

The invention claimed is:

1. A telescopic lifting unit, comprising:
a first segment, a second segment, and a third segment;
said first and second segments being mounted for displacement relative to one another;
said second and third segments being mounted for displacement relative to one another;
a motor unit configured to move said first and second segments relative to one another, said motor unit being configured to interact with a spindle to convert a rotational movement of a motor of said motor unit into a translational movement between said first and second segments; and
a cable hoist configured to move said second and third segments relative to one another.

2. The telescopic lifting unit according to claim 1, configured as a part of a mobile medical apparatus.

3. The telescopic lifting unit according to claim 1, incorporated into a mobile X-ray apparatus.

4. The telescopic lifting unit according to claim 3, wherein one of said first, second, or third segments is configured to have an X-ray head fastened thereto.

5. The telescopic lifting unit according to claim 3, wherein said one of said first, second, or third segments forms a load-bearing segment having a linear guide for displacing the X-ray head.

6. The telescopic lifting unit according to claim 1, wherein one of said first, second, or third segments is configured to have a load fastened thereto.

7. The telescopic lifting unit according to claim 6, wherein said one of said first, second, or third segments forms a load-bearing segment having a linear guide for displacing the load.

8. The telescopic lifting unit according to claim 1, wherein a movement of said first and second segments relative to one another, and a movement of said second and third segments relative to one another, are synchronized.

9. The telescopic lifting unit according to claim 1, wherein said motor unit has a first displacement speed and said cable hoist has a second displacement speed, and wherein the first displacement speed is greater than the second displacement speed.

10. The telescopic lifting unit according to claim 1, wherein said motor unit and/or said cable hoist has a weight compensation device.

11. The telescopic lifting unit according to claim 1, wherein said cable hoist has a weight compensation device adapted to receive a cable of said cable hoist.

12. The telescopic lifting unit according to claim 1, further comprising a force sensor.

* * * * *

UNITED STATES PATENT AND TRADEMARK OFFICE
CERTIFICATE OF CORRECTION

| | | |
|---|---|---|
| PATENT NO. | : 11,697,576 B2 | |
| APPLICATION NO. | : 16/684032 | |
| DATED | : July 11, 2023 | |
| INVENTOR(S) | : Daniel Greilinger et al. | |

It is certified that error appears in the above-identified patent and that said Letters Patent is hereby corrected as shown below:

On the Title Page

Please insert the following:
--(30) Foreign Application Priority Data
Nov. 14, 2018 (DE) ................... 10 2018 219 404. 1--

Signed and Sealed this
Fifteenth Day of August, 2023

Katherine Kelly Vidal
*Director of the United States Patent and Trademark Office*